US012731677B2

(12) United States Patent
Gering et al.

(10) Patent No.: US 12,731,677 B2
(45) Date of Patent: Sep. 8, 2026

(54) POINT-OF-CARE MEDICAL ANALYZER CONSUMABLE AVAILABILITY PREDICTION

(71) Applicant: Radiometer Medical ApS, Bronshoj (DK)

(72) Inventors: Henrik Jepsen Gering, Bronshoj (DK); Halina Tomaszewska, Bronshoj (DK)

(73) Assignee: Radiometer Medical ApS (DK)

(*) Notice: Subject to any disclaimer, the term of this patent is extended or adjusted under 35 U.S.C. 154(b) by 785 days.

(21) Appl. No.: 17/051,198

(22) PCT Filed: May 2, 2019

(86) PCT No.: PCT/EP2019/061218
§ 371 (c)(1),
(2) Date: Oct. 28, 2020

(87) PCT Pub. No.: WO2019/211365
PCT Pub. Date: Nov. 7, 2019

(65) Prior Publication Data

US 2021/0241888 A1 Aug. 5, 2021

(30) Foreign Application Priority Data

May 4, 2018 (DK) ........................... PA 2018 00196

(51) Int. Cl.
*G06Q 10/00* (2026.01)
*G06N 20/00* (2019.01)
(Continued)

(52) U.S. Cl.
CPC ............. *G16H 40/20* (2018.01); *G06N 20/00* (2019.01); *G16H 10/40* (2018.01); *G16H 40/40* (2018.01); *G16H 50/20* (2018.01); *G16H 50/70* (2018.01)

(58) Field of Classification Search
CPC ........ G16H 40/20; G16H 10/40; G16H 50/20; G16H 40/40
See application file for complete search history.

(56) References Cited

U.S. PATENT DOCUMENTS 11,416,810 B2 * 8/2022 Fredrich ................ G06Q 10/04
2005/0014285 A1 1/2005 Miller
(Continued)

FOREIGN PATENT DOCUMENTS

CN 105866453 A 8/2016
JP 2002-32642 A 1/2002
(Continued)

OTHER PUBLICATIONS

International Search Report for International Application No. PCT/EP2019/061218, Aug. 2, 2019.
(Continued)

*Primary Examiner* — Rajesh Khattar
(74) *Attorney, Agent, or Firm* — FBT Gibbons LLP

(57) ABSTRACT

Disclosed herein are apparatus for generating predicted consumable state data of a point-of-care medical analyzer comprising an input unit and a processing unit. Also disclosed are methods for generating predicted consumable state data of a point-of-care medical analyzer comprising receiving initial consumable state data of a point-of-care medical analyzer defining an initial amount of a point-of-care medical analyzer consumable present in the point-of-care medical analyzer, and an analyzer identifier at a first time index, receiving a second time index, and generating predicted consumable state data defining an amount of the point-of-care medical analyzer consumable predicted to be present in the point-of-care medical analyzer at the second time index using a predicted consumable depletion model selected using at least the analyzer identifier and the initial consumable state data. Additionally disclosed are systems
(Continued)

comprising at least one point-of-care medical analyzer, an apparatus as disclosed herein, and a data communications network.

20 Claims, 5 Drawing Sheets

(51) Int. Cl.

| | |
|---|---|
| ***G16H 10/40*** | (2018.01) |
| ***G16H 40/20*** | (2018.01) |
| ***G16H 40/40*** | (2018.01) |
| ***G16H 50/20*** | (2018.01) |
| ***G16H 50/70*** | (2018.01) |

(56) References Cited

U.S. PATENT DOCUMENTS

2007/0118422 A1 5/2007 Berger et al.
2018/0068263 A1 3/2018 Ginster, II et al.
2020/0232999 A1* 7/2020 Postma ............ G01N 35/00663
2023/0003633 A1* 1/2023 Hammond ......... G01N 15/1429

FOREIGN PATENT DOCUMENTS

JP 2007-524080 A 8/2007
JP 2008-180640 A 8/2008
JP 2009-162584 A 7/2009
JP 2010-107368 A 5/2010
JP 2011-209275 A 10/2011
JP 2012-237734 A 12/2012
JP 2012-243324 A 12/2012
WO WO 2017/221386 A1 12/2017

OTHER PUBLICATIONS

Written Opinion of the International Searching Authority for International Application No. PCT/EP2019/061218.

* cited by examiner

100

102

104

150a
150b
150c
150d
001
002
003
004
150
158
154
152
b) 3d, 6h
160
a) 1d, 4h
a)
b)
156

164
%
Mo 80%
Th 75%
We 60%
Th 40%
Fr 35%
Sa 32%

168
180
170
182
184
172
178
174
176a
176b

POINT-OF-CARE MEDICAL ANALYZER CONSUMABLE AVAILABILITY PREDICTION

This application is a national stage filing under 35 U.S.C. § 371 of International Application No. PCT/EP2019/061218, filed on May 2, 2019, which claims priority of Danish Patent Application No. PA 2018 00196, filed on May 4, 2018. The contents of these applications are each incorporated herein by reference.

FIELD OF THE INVENTION

This invention relates generally to an apparatus for generating predicted consumable state data of a point-of-care medical analyzer, a method for generating predicted consumable state data of a point-of-care medical analyzer, a system, a computer program element, and a computer readable medium.

BACKGROUND

Automatic point-of-care medical analyzers have almost replaced manual testing opera-tions in hospitals, in diagnostic test centres, and at the point-of-care (POC). Such devices can, for example, be used for blood gas testing, urea testing, diabetes management, and haematology.

For example, a typical high-performance blood-gas analyzer tests for a wide variety of electrolytes, metabolites, and biomarkers such as pCO2, pO2, pH, Na+, K+, Ca2+, Cl−, glucose, lactate, and haemoglobin, D-dimer, Troponin, CKMB, Myoglobin, NT-proBNP, CRP, BhCG, PCT amongst others. A typical automatic blood-gas analyzer can achieve a throughput of around 30 samples per hour, with multiple blood tests in a single sample, providing a total of around 300 tests per hour.

Such automatic point-of-care medical analyzers require a range of reagents. Typically, in a diagnostic test centre or a large hospital, a large number and a variety of types of automatic point-of-care medical analyzers are present, complicating the efficient management of reagents.

In some situations one or more persons may be assigned the task of keeping the point-of-care testing devices up and running. These persons monitor that the devices are always calibrated, have performed the scheduled Quality Control, and have sufficient consumables. These point-of-care coordinators do not regularly use the analyzer and therefore does not know the consumable state from hour-to-hour. Hence, they often rely on input from the operators, which are usually the nurses, as to status of consumable for each analyzer. To make sure that the point-of care analyzer is always up and running, the nurses may call the point-of-care coordinator well in advance of the analyzer running out of consumable, to make sure that the consumable is replaced and the point-of-care testing device is always ready to use. This often leads to replacement of consumables before it is necessary to replace the consumable, and therefore leads to waste.

US 2003/0172009 A1 discusses a consumables supply management system in which clinical test analysis devices in medical institutions and a computer of a consumables supplier are connected via a communication line. However, such systems can be further improved.

Therefore, an improved reagent management approach for automatic point-of-care medical analyzers is required.

SUMMARY OF THE INVENTION

It would be advantageous to have an improved technique for point-of-care medical analyzer consumable availability prediction. The object of the present invention is solved by the subject-matter of the independent claims, wherein further embodiments are incorporated in the dependent claims.

An apparatus for generating predicted consumable state data of a point-of-care medical analyzer comprising:

an input unit; and a processing unit.

The input unit is configured to receive initial consumable state data of a point-of-care medical analyzer defining an initial amount of a point-of-care medical analyzer consumable present in the point-of-care medical analyzer, and an analyzer identifier at a first time index.

The input unit is configured to receive a second time index.

The processing unit is configured to generate predicted consumable state data defining an amount of the point-of-care medical analyzer consumable predicted to be present in the point-of-care medical analyzer at the second time index using a predicted consumable depletion model selected using at least the analyzer identifier and the initial consumable state data.

The predicted consumable depletion model comprises (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test.

The predicted consumable state data is generated by the processing unit based on an aggregation of the initial amount of a point-of-care medical analyzer consumable present in the point-of-care medical analyzer, and the outputs of at least the consumable model and the a point-of-care medical analyzer use model between the first time index and the second time index, and the location of the point-of-care medical analyzer.

Advantageously, it is possible to quickly and automatically generate a predicted future consumable state of one, or many, consumables in a point-of-care medical analyzer taking into account the complexities of individual test protocols, and data concerning how frequently the point-of-care medical analyzer is used.

Optionally, the apparatus is configured to receive historic usage data of the point-of-care medical analyzer defined by the analyzer identifier.

Advantageously, a point-of-care medical analyzer, or a networked computer in communication with the point-of-care medical analyzer may provide predicted consumable state data having increased accuracy because the level of consumable at a certain historical month, week, day, or even time may be used to improve the accuracy of the predicted consumable state data.

Optionally, the apparatus is configured to receive a consumable usage rule set defining the consumption of the point-of-care medical analyzer consumable over time.

Advantageously, a forward-looking set of predictive rules defining consumable usage may be used to improve the accuracy of the predicted consumable state data. For example, a preset for a specific blood-gas analyzer may be provided with a rule set that specifies on every Friday, an increased number of blood-gas tests are performed in accordance with a regular timetable of a hospital.

Optionally, the apparatus is configured to receive a consumable capacity metric of the point-of-care medical analyzer consumable using the analyzer identifier.

Optionally, the apparatus is configured to generate the consumable model based on at least one of the historic usage data, the consumable usage rule set, a consumable handling model of the point-of-care medical analyzer, and the consumable capacity metric of the point-of-care medical analyzer identified by the analyzer identifier and running from the initial consumable state data collected at the first time index. Advantageously, combination of several information sources enables a more accurate assessment of the amount of a point-of-care medical analyzer consumable remaining in a point-of-care medical analyzer at a second time index.

Optionally, the consumable model of the point-of-care medical analyzer comprises a linear model, a rule-based machine learning system, experimentally fitted data, and/or a Bayesian model.

Advantageously, a wide range of appropriate data analysis models may be provided to suit the point-of-care medical analyzer network employed. For example, a hospital department with a relatively invariant caseload (in other words, with a well-defined schedule of testing) may prioritise a rule-based or linear model. A large hospital could use experimentally fitted data, and/or a Bayesian model to define the incidence of medical tests caused by seasonally appearing illnesses, for example.

Optionally, the apparatus is configured to receive usage pattern data of the point-of-care medical analyzer defined by the analyzer identifier obtained before the first time index.

Advantageously, a historical model of consumable depletion may be generated from usage pattern data which accurately characterises a historical use of a specific point-of-care medical analyzer installed in a hospital or clinic Optionally, the apparatus is configured to receive usage location metadata of the point-of-care medical analyzer defined by the analyzer identifier.

Optionally, the apparatus is configured to receive a future usage plan of the point-of-care medical analyzer defined by the analyzer identifier between the first time index and the second time index.

Optionally, the apparatus is configured to generate the point-of-care medical analyzer use model based on at least one of the usage pattern data, usage location metadata, and the future usage plan.

Optionally, the point-of-care medical analyzer use model outputs an expected number of tests between the first and second time indexes.

Optionally, aggregating the outputs of at least the consumable model and the point-of-care medical analyzer use model between the first time index and the second time index comprises calculating a test depletion of a point-of-care medical analyzer consumable in the point-of-care medical analyzer for a test, and multiplying the test depletion by the expected number of tests to generate the predicted consumable state data at the second time index, and/or as a variable between the first time index and the second time index.

Advantageously, it is possible for a user to define a time window during which a prediction of the consumable present in a point-of-care medical analyzer, and the depletion of the consumable, is required. For example, a point-of-care medical analyzer technician could define a time window corresponding to their holiday. The use model would provide an expected number of tests between the first and second time indexes whilst the point-of-care medical analyzer technician was absent. In turn, would then be possible to predict at what time index a point-of-care medical analyzer in the care of the point-of-care medical analyzer technician became fully depleted of a significant reagent. The point-of-care medical analyzer technician would be able to predict, before leaving for their holiday, when refill of a given reagent would be required.

Optionally, the apparatus is configured to receive expiry date data of the point-of-care medical analyzer consumable, and to include the point-of-care medical analyzer consumable as a factor in the consumable model only between the first time index and an expiry date defined in the expiration date data.

Optionally, the apparatus further comprises:

- a data output unit. The data output unit is configured to output the predicted consumable state data at the second time index, and/or as a variable between the first time index and the second time index.

Optionally, the apparatus further comprises an output display.

The output display is configured to display a GUI comprising a representation of the point-of-care medical analyzer, and the initial amount of the point-of-care medical analyzer consumable present in the point-of-care medical analyzer, to receive from a user the second time index via the GUI interface, and to display an indication of how urgently a replacement of the point-of-care medical analyzer consumable present in the point-of-care medical analyzer is required on the GUI at the second time index.

Advantageously, a user may quickly and simply input time durations during which one or more point-of-care medical analyzers are used without maintenance staff, for example. The GUI produced quickly enables managers to assess the remaining capacity of the one or more point-of-care medical analyzers to provide a series of tests. Furthermore, the GUI can use the modelling described herein to provide a prediction of various configuration arrangements of a medical analysis system. For example, a user could investigate whether taking first and second point-of-care medical analyzers off-line would enable remaining stocks of reagent to keep a certain point-of-care medical analyzer running for a longer time.

Optionally, the apparatus is configured to display on the GUI a plurality of representations each corresponding to a unique point-of-care medical analyzer of a plurality of point-of-care medical analyzers, to receive from a user the second time index via the GUI interface, and to sort the plurality of representations in the GUI based on the level of urgency of replacement of the point-of-care medical analyzer consumable for each of the point-of-care medical analyzers of a plurality of point-of-care medical analyzers.

Optionally, the apparatus is configured to generate and display a list of consumables and/or the amount of consumables for replenishment of point-of-care medical analyzers in the plurality of point-of-care medical analyzers.

Optionally, the apparatus is a blood-gas analyzer.

According to a second aspect, there is provided a method for generating predicted consumable state data of a point-of-care medical analyzer, comprising:

- receiving initial consumable state data of a point-of-care medical analyzer defining an initial amount of a point-of-care medical analyzer consumable present in the point-of-care medical analyzer, and an analyzer identifier at a first time index;
- receiving a second time index;
- generating predicted consumable state data defining an amount of the point-of-care medical analyzer consumable predicted to be present in the point-of-care medical analyzer at the second time index using a predicted consumable depletion model selected using at least the analyzer identifier and the initial consumable state data;
- wherein the predicted consumable depletion model comprises (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test; and wherein the predicted consumable state data is generated based on an aggregation of the initial amount of a point-of-care medical analyzer consumable present in the point-of-care medical analyzer, and the outputs of at least the consumable model and the a point-of-care medical analyzer use model between the first time index and the second time index.

Optionally, the method comprises receiving historic usage data of the point-of-care medical analyzer defined by the analyzer identifier.

Optionally, the method comprises receiving a consumable usage rule set defining the consumption of the point-of-care medical analyzer consumable over time.

Optionally, the method comprises receiving a consumable capacity metric of the point-of-care medical analyzer consumable using the analyzer identifier.

Optionally, the method comprises generating the consumable model based on at least one of the historic usage data, the consumable usage rule set, a consumable handling model of the point-of-care medical analyzer, and the consumable capacity metric of the point-of-care medical analyzer identified by the analyzer identifier and running from the initial consumable state data collected at the first time index.

Optionally, in the method the consumable model of the point-of-care medical analyzer comprises a linear model, a rule-based machine learning system, experimentally fitted data, and/or a Bayesian model.

Optionally, the method comprises receiving usage pattern data of the point-of-care medical analyzer defined by the analyzer identifier obtained before the first time index.

Optionally, the method comprises receiving usage location metadata of the point-of-care medical analyzer defined by the analyzer identifier.

Optionally, the method comprises receiving a future usage plan of the point-of-care medical analyzer defined by the analyzer identifier between the first time index and the second time index.

Optionally, the method comprises generating the point-of-care medical analyzer use model based on at least one of the usage pattern data, usage location metadata, and the future usage plan.

Optionally, in the method the point-of-care medical analyzer use model outputs an expected number of tests between the first and second time indexes.

Optionally, in the method aggregating the outputs of at least the consumable model and the point-of-care medical analyzer use model between the first time index and the second time index comprises:

calculating a test depletion of a point-of-care medical analyzer consumable in the point-of-care medical analyzer for a test, and multiplying the test depletion by the expected number of tests to generate the predicted consumable state data at the second time index, and/or as a variable between the first time index and the second time index.

Optionally, in the method receiving expiry date data of the point-of-care medical analyzer consumable including the point-of-care medical analyzer consumable as a factor in the consumable model only between the first time index and an expiry date defined in the expiration date data.

Optionally, the method comprises outputting the predicted consumable state data at the second time index, and/or as a variable between the first time index and the second time index.

Optionally, the method comprises displaying a GUI comprising a representation of the point-of-care medical analyzer, and the initial amount of the point-of-care medical analyzer consumable present in the point-of-care medical analyzer.

Optionally, the method comprises displaying an indication of how urgently a replacement of the point-of-care medical analyzer consumable present in the point-of-care medical analyzer is required on the GUI at the second time index.

Optionally, the method comprises displaying on the GUI a plurality of representations each corresponding to a unique point-of-care medical analyzer of a plurality of point-of-care medical analyzer, receiving from a user the second time index via the GUI interface, sorting the plurality of representations in the GUI based on the level of urgency of replacement of the point-of-care medical analyzer consumable for each of the point-of-care medical analyzers of a plurality of point-of-care medical analyzers.

Optionally, the method comprises generating a list of consumables and/or the amount of consumables for replenishment of point-of-care medical analyzers in the plurality of point-of-care medical analyzers.

According to a third aspect, there is provided a system comprising:

a point-of-care medical analyzer;

an apparatus according to the first aspect or one of its embodiments; and a data communications network.

The point-of-care medical analyzer is configured to transmit to the apparatus, via the data communications network, initial consumable state data of a point-of-care medical analyzer defining an initial amount of a point-of-care medical analyzer consumable present in the point-of-care medical analyzer, and an analyzer identifier at a first time index.

Optionally, the system comprises:

a mobile data terminal.

The mobile data terminal is configured to:

display a GUI comprising a representation of the point-of-care medical analyzer, and the initial amount of the point-of-care medical analyzer consumable present in the point-of-care medical analyzer;

transmit to the apparatus, via the data network, the second time index via the GUI interface;

receive response data from the apparatus; and display an indication of how urgently a replacement of the point-of-care medical analyzer consumable present in the point-of-care medical analyzer at the second time index is required on the GUI of the mobile device.

Optionally, the system is provided wherein the at least one point-of-care medical analyzer is configured to identify an installed point-of-care medical analyzer consumable using a point-of-care medical analyzer consumable identifier and the at least one point-of-care medical analyzer is configured to transmit an intermediate amount of a point-of-care medical analyzer consumable present in the installed point-of-care medical analyzer consumable over the data communications network in association with the point-of-care medical analyzer consumable identifier.

According to a fourth aspect, there is provided a computer program element comprising instructions which, when executed by a computer, enables the computer to carry out the method according to the second aspect and its embodiments.

According to a fifth aspect, there is provided a computer program product, tangibly embodied on a carrier medium, comprising software code for carrying out the method according to the second aspect.

Point-of-care testing (POCT or bedside testing) is defined as medical diagnostic testing at or near the point-of-care—that is, at the time and place of patient care. This contrasts with the historical pattern in which testing was wholly or mostly confined to the medical laboratory, which entailed sending off specimens away from the point-of-care and then waiting hours or days to learn the results, during which time care must continue without the desired information.

The driving notion behind POCT is to bring the test conveniently and immediately to the patient. This increases the likelihood that the patient, physician, and care team will receive the results quicker, which allows for better immediate clinical management decisions to be made. POCT includes: blood glucose testing, blood gas and electrolytes analysis, rapid coagulation testing, rapid cardiac markers diagnostics, drugs of abuse screening, urine strips testing, pregnancy testing, fecal occult blood analysis, food pathogens screening, hemoglobin diagnostics, infectious disease testing and cholesterol screening.

POCT is often accomplished through the use of transportable, portable, and handheld instruments. Small bench analyzers or fixed equipment can also be used when a handheld device is not available—the goal is to collect the specimen and obtain the results in a very short period of time at or near the location of the patient so that the treatment plan can be adjusted as necessary before the patient leaves. Cheaper, faster, and smarter POCT devices have increased the use of POCT approaches by making it cost-effective for many diseases. Additionally, it is very desirable to measure various analytes simultaneously in the same specimen, allowing a rapid, low-cost, and reliable quantification. Therefore, multiplexed point-of-care testing (xPOCT) has become more important for medical diagnostics in the last decade.

In the following application, the term "predicted consumable state data" is a data structure that may be stored in volatile/or non-volatile storage media (such as computer RAM, or a hard drive, respectively) defining a predicted level of depletion of one, or more reagents remaining within a point-of-care medical analyzer at a given time index, taking into account number of medical tests performed within a time range preceding the given time index, and the amount of reagent used for a certain type of test.

For example, the data structure may comprise numerical elements as fixed or floating point numbers providing a remaining fluid quantity, per reagent of the analyzer, in millilitres. Optionally, the data structure may comprise numerical elements as floating point numbers or integers representing a percentage of a reagent remaining.

Furthermore, the predicted consumable state data may be a single value (providing a snapshot of reagent depletion at one time), or the predicted consumable state data may be an N-dimensional state vector defining a predicted remaining reagent quantity, per reagent type used in the analyzer, at a number of time points in the future.

Optionally, one or more numerical elements of the predicted consumable state data may comprise a statistical measure, such as a likelihood that a given volume level is reached at a certain time index. Optionally, one or more numerical elements of the predicted consumable state data may comprise a predicted range of volumes that may be obtained with a given probability. For example, the predicted consumable state data additionally comprises a volume range spanning an average predicted consumable level, wherein the volume range defines a 5%, 10%, 20%, 30%, 40%, or 50% likelihood that the lower and/or upper portion of the volume range is reached.

In the following application, the term "initial consumable state data" represents automatically digitised fluid volume or reagent quantity data obtained by an electronic measurement means of a point-of-care medical analyzer such as a photodiode or phototransistor level monitoring device, or an ultrasonic fluid level monitoring device. The initial consumable state data may be transmitted automatically by the point-of-care medical analyzer, or an apparatus monitoring the point-of-care medical analyzer may "poll" a point-of-care medical analyzer at will for the level information.

In the following application, the term "analyzer identifier" refers to a code or serial number which uniquely identifies a point-of-care medical analyzer on a computer network comprising a plurality of point-of-care medical analyzers, so that initial consumable state data read from the uniquely identified point-of-care medical analyzer can be used to predict the future reagent state of that uniquely identified point-of-care medical analyzer in the future.

In the following application, the term "time index" refers to a data object enabling, for example, consumable state to be defined according to a time. Many different types of time format may be used, with resolutions of seconds, minutes, hours, days, or weeks dependent upon the application of the point-of-care medical analyzer.

In the following application, the term "predicted consumable depletion model" refers to a computer-implemented algorithm functioning to predict the depletion of one or more reagents in a unique point-of-care medical analyzer over a time range. The "predicted consumable depletion model" comprises at least two elements: a "consumable model" defining an amount of one or more reagents expended during the implementation of a defined test, and a "point-of-care medical analyzer use model" defining how many tests occur in between a first and a second time index.

The "consumable model" is, in the simplest case, parameterised by the number of tests of a specific type which are formed. The output of the "consumable model" for a given number of tests performed defines a total consumption (for example, in millilitres) of one or a plurality of reagents defined by a protocol required for an implementation of a particular test (such as a test for pCO2, pO2, pH, Na+, K+, Ca2+, Cl−, glucose, lactate, or haemoglobin, amongst others). The consumable model may optionally account for variations of the particular test (in particular, it may account for differing volumes of reagent required for different volumes of blood, for example). Optionally, the consumable model may define volume of reagent delivered statistically—in other words by providing the desired volume of reagent as an average of a probability distribution such as the normal distribution, and defining a variation in the amount of reagent delivered to a patient according to the standard deviation of the normal distribution. It will be appreciated that modern point-of-care medical analyzers are somewhat accurate in their ability to monitor the volume of a reagent delivered. However, in the context of long-term frequent use of a point-of-care medical analyzer, even small deviations from an expected average reagent amount delivered per test may build up into a significant error between the expected and actual amount of reagent remaining in the point-of-care medical analyzer.

Optionally, the "consumable handling model of the point-of-care medical analyzer" is would include a model of the volume of the fluid handling system of the point-of-care medical analyzer, including data from the liquid transport system showing how many mL of liquid has been withdrawn from the pouches. The liquid transport system includes a pump, valves controlling which pouch liquid is drawn from, and thus which liquid is introduced into the measuring chamber.

To take account of cases where the same point-of-care medical analyzer may perform a plurality of different test, the term "consumable model" is optionally a composite of a plurality of "consumable sub-models", with each consumable sub-model representing one of a plurality of unique tests that may be performed on the same point-of-care medical analyzer.

The "point-of-care medical analyzer use model" refers to a computer—in the amended algorithm defining the use of a given type of point-of-care medical analyzer over a time in-between the first and the second time index. The point-of-care medical analyzer use model provides an accurate impression of the number and type of tests applied using a given point-of-care medical analyzer. Of course, the use of a single point-of-care medical analyzer may be defined by a wide range of factors, some of which may be enumerates without limitation as: whether or not a given point-of-care medical analyzer is located in a specialised medical testing centre, a large point-of-care location such as a hospital, or a small point-of-care location such as a doctor's surgery (point-of-care medical analyzer location) will reflect in the rate at which the point-of-care medical analyzer is used. The department in which the point-of-care medical analyzer is placed, along with whether or not it is located with other point-of-care medical analyzers of the same type can have an effect on usage intensity. Utilisation of a point-of-care medical analyzer may vary dependent on a portion of a day, week, month, or even year. For example, a medical testing centre may be configured to analyse a large number of samples according to a set timetable (for example, a given number of blood gas tests on every recurring Friday). Optionally, these trends may be pre-programmed. Optionally, such trends may be observed using a simple straight-line statistical model or more advanced Bayesian inference or machine learning. To summarise, the point-of-care medical analyzer use model optionally provides a statistically inferred number and type of tests applied using a given point-of-care medical analyzer in between a first and a second time index. Optionally, the point-of-care medical analyzer use model may apply historically recorded point-of-care medical analyzer use records, under the assumption that future use is similar to past use.

In the following application, the term "aggregation" refers to the combination of the "initial consumable state data", and respective outputs of the "consumable model" and the "point-of-care medical analyzer use model" in order to provide an absolute or a statistically qualified estimate of one or more reagents remaining in a given point-of-care medical analyzer at a second time index.

In a simple case, a user would desire to know an amount of distilled water remaining in a point-of-care medical analyzer over one week of use. The user would input into the "predicted consumable depletion model" the specific future dates as first and second time indexes. The point-of-care medical analyzer would be interrogated to reveal that 1000 mL of distilled water remained (initial consumable state data). A point-of-care medical analyzer use model would define that in between the first and second time indexes (such as one week) 10 tests of a given protocol requiring distilled water would be required according, for example, to historical use data. The "consumable model" would reveal that for the given protocol, each iteration of the protocol required 20 mL of distilled water. Thus, the aggregation in this case would be multiplication of the total number of tests by the total amount of distilled water required for each test. As the out-come of the 10 tests would still leave enough distilled water for future tests to be con-ducted, predicted consumable state data output would reflect the final amount. The skilled person will appreciate that the preceding example is a basic example, and that many analysis protocols require 2 to 10 reagents, all having different depletion rates which are difficult to track. In the case of a consumable model and a point-of-care medical analyzer use model that are defined according to continuous random variables, for example, the process of aggregation is more complicated than the multiplication discussed above and may, for example, apply Bayesian inference defining the "predicted consumable state data" in terms of prior knowledge of the use of the point-of-care medical analyzer.

In the following application, the term "historic usage data" means a recorded reagent consumption trend with respect to time of a uniquely identified point-of-care medical analyzer, or for a type of point-of-care medical analyzer similar to the analyzer that is uniquely identified.

In the following application, the term "consumable usage rule set" defines a volume of one or more consumables (reagents) used for one, or more tests. A more complicated rule set may define statistical variations of the consumable usage for significant numbers of tests.

In the following application, the term "usage location data" may define a department or hospital that the point-of-care medical analyzer is used in. The consumable model may optionally correlate the "usage location data" with historically stored reagent depletion models, so that as analyzers are repositioned within a point-of-care the predicted consumable state data remains accurate.

Furthermore, the usage location is valuable when the Point-of-Care Coordinator should exchange the consumable or replenish the local consumable storage.

As the point-of-care medical analyzer may be moved around, the location of the analyzer may be derived dynamically in the system based on well-known positioning methods. Alternatively, the location may be manually entered into the system as a specific department of the hospital or a certain floor of the hospital, which may not give the exact location, but a defined area where to look for it.

In the following application, the term "future usage plan" is a data structure defining a number and type of tests performed between at least the first and second time indexes. This data is preferably drawn from an automated hospital control system (operating on a hospital server, for example). In other words, as healthcare professionals request appointments for the various medical tests (such as blood tests) on a large number of patients, the point-of-care medical analyzer use model is updated with the future usage plan data. Optionally, the predicted consumable depletion model in this case reduces the statistical significance of a predicted point-of-care medical analyzer use model, and emphasises the future usage plan data within the model, because the future usage plan data is a more reliable source of information about the usage of a point-of-care medical analyzer. Optionally, the future usage plan may be continuously updated from a wide range of locations, such as a plurality of small surgeries, and/or multiple hospitals. Accordingly, a more accurate estimate of the predicted consumable state data can be provided. Accordingly, it is a basic idea of the invention to aggregate information relating to the projected number of activities on particular a point-of-care medical analyzer and the activity types, with model of how one activity on an analyzer translates into consumable usage. This enables a prediction to be formed of future reagent levels inside point-of-care medical analyzers, as well as optionally the probabilities of the predictions being correct. These predictions and probabilities may be presented to a user in a clear and user-friendly way on a graphical user interface (GUI).

BRIEF DESCRIPTION OF THE FIGURES

Exemplary embodiments of the invention will be described in the following schematic drawings, which are not presented to scale.

DETAILED DESCRIPTION OF EMBODIMENTS

Figure 1A:
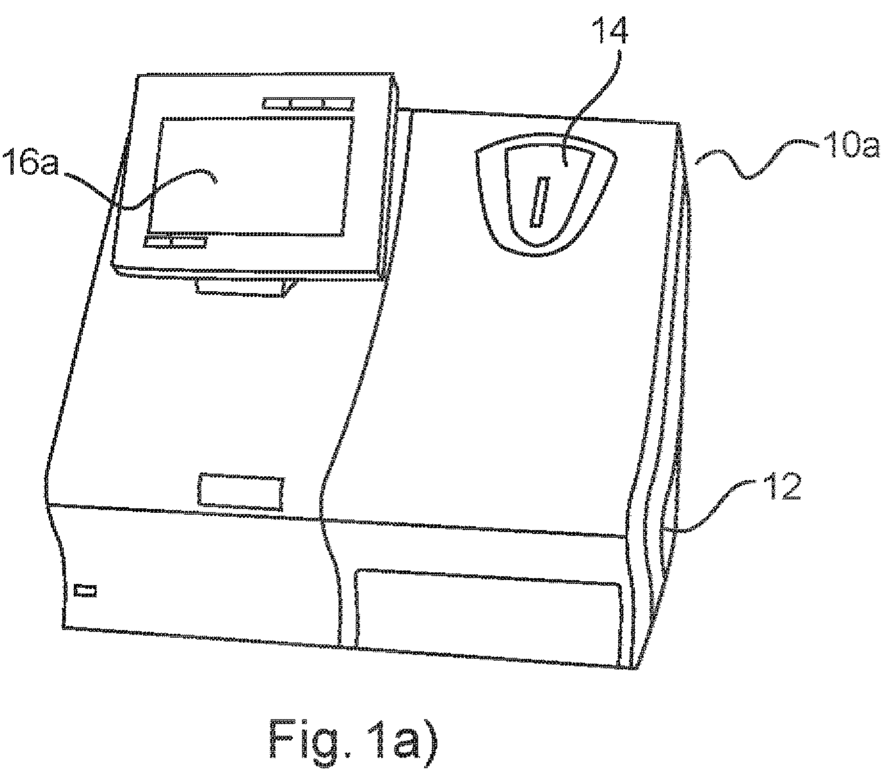
FIG. 1*a*) schematically illustrates a medical diagnostic apparatus.

FIG. 1*a*) illustrates a medical analysis apparatus 10*a*. The medical analysis apparatus 10*a* comprises an enclosure 12 with a portal 14 suitable for receiving a test container containing a body fluid sample (such as a blood sample) taken from a patient, such as a vacutainer or a capillary tube (not shown) optionally, the portal may allow the injection of sampled blood directly from a test syringe. The medical analysis apparatus 10*a* further comprises a display screen 16*a* for illustrating the progress of a blood-gas test, for example. A plurality of the reagent fluids used in the test are provided by replaceable cartridges, sealed bags, or bottles (not shown). Another example of a consumable used by a medical analysis apparatus 10*a* is a “sensor cassette” of replaceable functional sensors which are used to contact a sample from a patient. Typically, the sensors of the “sensor cassette” contain sensors comprising rare metal alloys (such as vanadium bronze) and functionalized with membranes holding active ingredients. Eventually, after several thousand uses, for example, such a “sensor cassette” may also need to be replaced.

In use, a user of the medical analysis apparatus 10*a* inserts a test container containing a blood sample, such as a whole-blood sample, into portal 14 and initiates the automatic test. In the course of the test, a proportion of the reagent fluids are depleted from their replaceable cartridges, sealed bags, and/or bottles. After several thousand tests, for example the sensors in a sensor cassette will be depleted. Eventually, the medical analysis apparatus will reach a point where it cannot perform further tests (or only a subset of tests) until the reagent fluids are replenished, or the sensor cassette is exhausted.

Figure 1B:
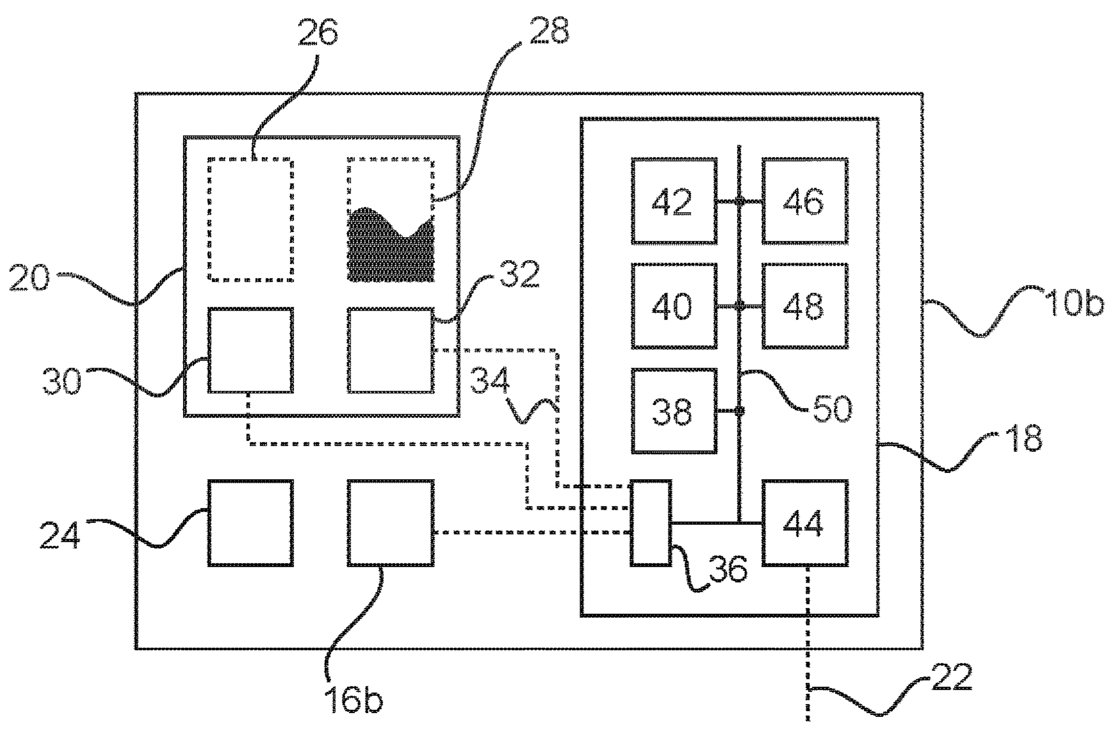
FIG. 1*b*) schematically illustrates a functional diagram of a medical diagnostic apparatus.

FIG. 1*b*) schematically illustrates a system diagram of the medical analysis apparatus 10*a* illustrated in FIG. 1*a*). In particular, the medical analysis apparatus 10*b* comprises an embedded computer 18, a testing subsystem 20, and external communications connection 22, a system power supply 24, and a display 16*b*.

The analysis subsystem 20 comprises a receptacle 26 in mechanical communication with portal 14, capable of accepting appropriately shaped test containers containing fluidic patient samples (such as blood, or blood plasma). The analysis subsystem 20 further comprises a reagent fluid supply 28. Optionally, the reagent fluid supply 28 is one, or a plurality of replaceable cartridges, or sealed bags (solution packs) engageable with a receptacle.

Optionally, the replaceable cartidges comprise data storage means readable by the processor 18 of the fluid analyzer 10. The data storage means may contain production date data, expiry data, and the production volume of liquid inside the pouch, and/or other metadata identifying the reagent, for example. Optionally, the data storage means may contain a cartridge identifier enabling the fluid analyzer 10 to interrogate a database over a data communications network for information about the reagent contained in a cartridge. Optionally, the data storage means is an optically readable indicator such as a QR code and/or a bar code. Optionally, the data storage means is an electrically readable indicator such as an RFID tag or an electronically connectable programmable memory element.

The reagent fluid supply 28 in the replaceable cartridge, or sealed bag may comprise one or a number of reservoirs pre-filled with process liquids (as known to a person skilled in the art: QC1, QC2, QC3, CAL3 (S1940), CAL2 (S1930), RINSE/CAL1 (S1920)) having a known composition. The skilled person will appreciate that other chemicals may be provided dependent on the exact test required.

Such a replaceable cartridge (not shown) may be equipped with a silicon rubber teat, for example, such that when brought into sealing engagement with the bottom of the receptacle, the replaceable cartridge is in fluid communication with the receptacle 26, enabling reagent fluid supply 28 comprised within the replaceable cartridge to flow into the receptacle 26. Alternatively, a membrane-piercing needle can be used to access the reagent. Optionally, the reagent fluid supply 28 comprises a fixed container, with a fluid suction assembly. The skilled person will appreciate that a network of fluid conduits, pumps, and the like enable the reagent fluid supply 28 to be carried into fluid communication with the receptacle.

The components of the analysis subsystem 20 are connected using a liquid transport system (not shown). In practice, a sub-sample of the patient sample of a few mL in volume, and/or the reagents from the reagent fluid supply 28, are transported around conduits of the analysis subsystem 20 separated by gas bubbles. Sensors comprised in the liquid transport subsystem detect and control the sequence of movements of sub-samples and reagents around the liquid transport subsystem to enable a sample analysis to take place.

The analysis subsystem 20 further comprises a test detector 30 (such as a vanadium bronze element supplemented with functionalized enzymes). The purpose of this unit is to observe the result of contacting the patient sample with the test detector 30 and thus to render a result of an analysis. For example, the test detector may comprise a sensor cassette-a mechanical array of a plurality of sensors (typically made, for example, from functionalized vanadium bronze) which is typically exposed to the patient blood sample and reagents several thousand times before it is exhausted.

Following an analysis of a sub-sample of the patient sample, the liquid transport system (not shown) transports the sub-sample of the patient sample and/or the expended reagent to a waste fluid collection vessel (not shown). Optionally, such a collection vessel be another container such as a separate pouch which is a modular part of the reagent solution pack.

The analysis subsystem 20 further comprises a reagent fluid supply monitoring unit 32. The purpose of this unit is to monitor the level of reagent fluid contained within the reagent fluid supply 28 (whether it is a replaceable cartridge, a bottle, or another type of receptacle).

Optionally, the reagent fluid supply monitoring unit 32 may use fluid level monitoring of a reagent receptacle to monitor a decline in the level of the reagent fluid supply 28 as the machine is used. For example, a photodiode, or phototransistor could be used. Optionally, ultrasound radar may be used to monitor the level of the reagent fluid supply. The skilled person will appreciate that many different types of level monitoring may be applied. The reagent fluid supply monitoring unit 32 digitises the reagent fluid supply level and transmits it to communication bus 34.

The medical analysis apparatus 10*a*, 10*b* further comprises an embedded computer 18. The purpose of the embedded computer is to coordinate the sequence of events that form a test on a patient sample, to communicate the result for further analysis, and to perform various housekeeping duties relevant to the medical analysis apparatus 10*a*, 10*b*, including the monitoring of fluid levels in the reagent fluid supply 28.

The embedded computer 18 comprises an internal input/output unit 36 for communi-cating with embedded hardware inside the medical analysis apparatus 10*a*, 10*b*. For example, the internal input/output unit 36 may be an "I2C" bus, a USB™ bus, or the like. The embedded computer 18 further comprises non-volatile memory 38 (such as an embedded hard-disk), volatile memory 40 (such as RAM), a display driver 42, an external input/output unit 44 (such as an Ethernet port), an input unit 46 (such as a key-board and/or touchscreen driver), and a processing unit 48 (such as an embedded Intel™ processor). These components are connected by a communications bus 50. The skilled person will appreciate the basic functions of these units, and that many variants and implementations exist.

In operation, the embedded computer 18 monitors the portal 14 for the presence of a sample via test detector 30. Simultaneously, the embedded computer 18 receives an (optionally real-time) digital representation of the fluid level in the reagent fluid supply 28 from the reagent fluid supply monitoring unit 32.

Accordingly, the embedded computer 18 may forward updates of the level of the reagent fluid supply 28 to an external network 22 or device via the external input/output unit 44. Optionally, the embedded computer 18 may forward updates of the level of the reagent fluid supply 28 more frequently as the level of the reagent fluid declines towards its lowest possible value.

Figure 2:
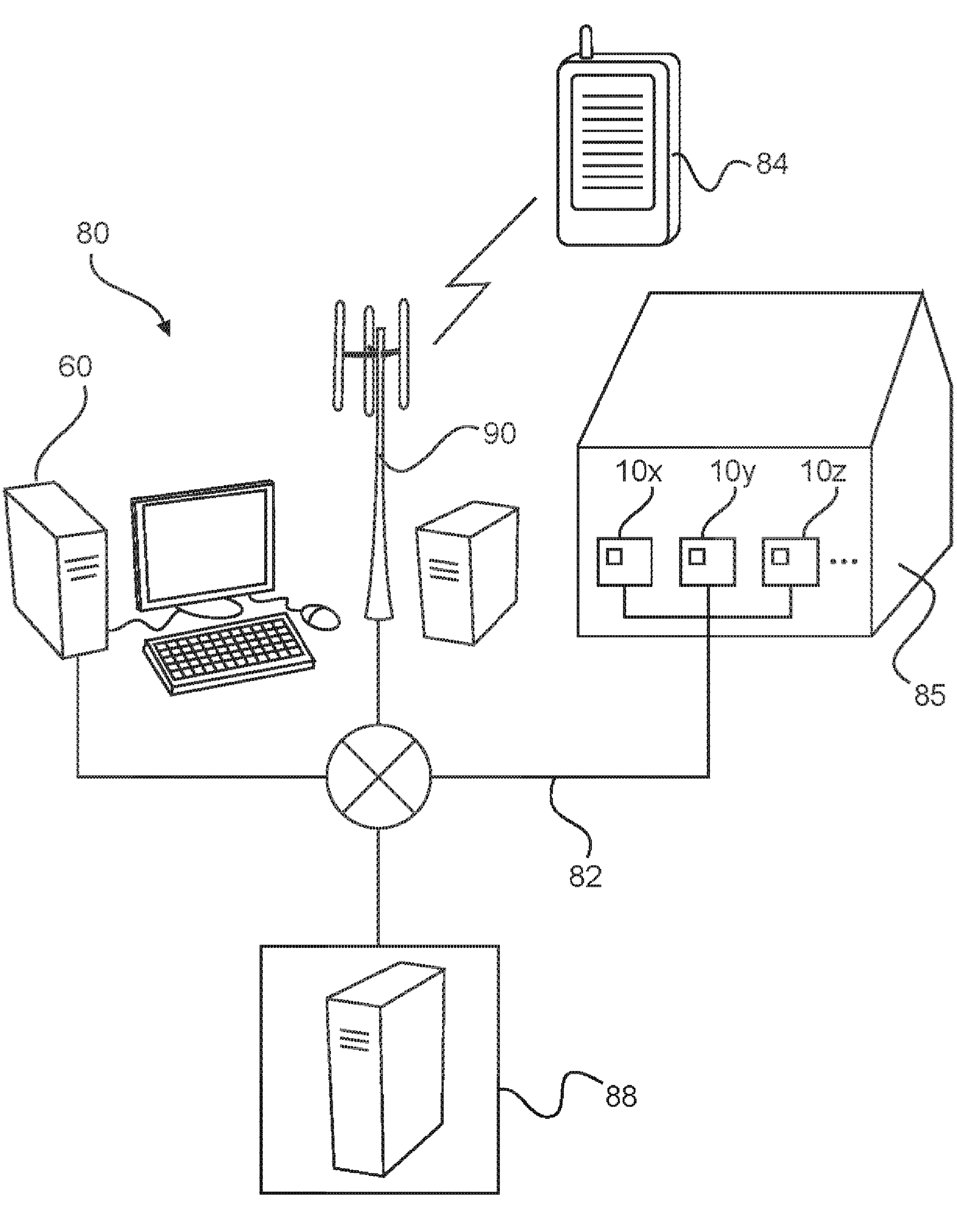
FIG. 2 schematically illustrates a system in accordance with the third aspect.

FIG. 2 illustrates a system 80 in accordance with the second aspect. The system 80 comprises a plurality of medical analysis apparatuses 10*x*, 10*y*, 10*z* each as described in connection with FIG. 1. The system also comprises an optional data warehouse (server, cloud server) 88, an optional mobile data device 84 (for example, a "smart phone" operating the iOS™ or the Android operating system), an optional wireless communication base station 90, and an apparatus 60 in accordance with the second aspect. All of these devices are communicatively coupled using a data communications network 82 (which conventionally may be a combination of LAN, WAN, WiFi™, GSM, LTE networks and the like). The operation of the system will be described later in the application.

It would ordinarily be difficult for a point-of-care coordinator to monitor the amount of a reagent remaining in each of medical analysis apparatuses 10*x*, 10*y*, 10*z*. Different point-of-care medical analyzers need to be refilled at different times, dependent on their use. The rate of reagent depletion depends at least upon the types of test operated on the medical analysis apparatuses, and the intensity of those tests. Such point-of-care medical analyzers are used at differing degrees of intensity dependent on whether they are installed in a busy town hospital, or a local clinic, dependent upon what time of year, and the like. Until now it has, therefore, been essentially impossible for a point-of-care coordinator accurately to predict future supply requirements for reagents used in such medical tests.

In use, apparatus 60 polls (or receives updates from) medical analysis apparatuses 10*x*, 10*y*, 10*z* located at a point-of-care or a testing facility 85. The medical analysis apparatuses 10*x*, 10*y*, 10*z* transfer data to the apparatus 60 over data communications network 82. Specifically, the medical analysis apparatuses 10*x*, 10*y*, 10*z* may transfer at least first, second, and third initial consumable state data to the apparatus 60 reflecting the respective reagent fill levels of the medical analysis apparatuses 10*x*, 10*y*, 10*z*. Optionally, point-of-care medical analyzer use information or measured consumable depletion rate information may also be transferred to the apparatus 60 for use in the calculation.

It will be appreciated by a skilled person that the medical analysis apparatuses 10*x*, 10*y*, 10*z* may be equipped with data processors powerful enough to generate predicted consumable state data themselves. In this case, predicted consumable state data (for example, the fluid level inside a reservoir), or the number of uses of the sensor element in the sensor cassette may be displayed on displays of the medical analysis apparatuses 10*x*, 10*y*, 10*z*, or forwarded to apparatus 60 or to mobile data device 84 to enable a point-of-care coordinator or technician to check on the overall status of medical analysis apparatuses 10*x*, 10*y*, 10*z* at the point-of-care 85. Optionally, medical analysis apparatuses 10*x*, 10*y*, 10*z* are configured to generate an order to a reagent supplier when an output of the predicted consumable depletion model indicates that reagent depletion is imminent, or that the sensor cassette is nearing the end of its predicted life-span. Accordingly, the order may be transmitted to the reagent supplier via the data communications network 82.

Figures 3, 4:
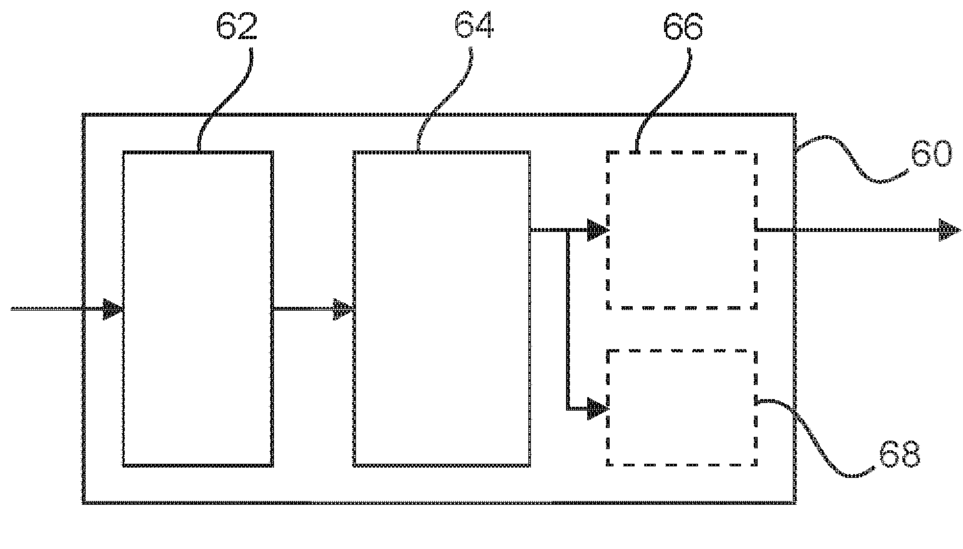
FIG. 3 schematically illustrates an apparatus in accordance with the first aspect.
FIG. 4 schematically illustrates a method in accordance with the second aspect.

FIG. 3 illustrates an apparatus 60 in accordance with the first aspect.

The first aspect comprises an apparatus 60 for generating predicted consumable state data of a point-of-care medical analyzer 10 comprising:

an input unit 62; and a processing unit 64.

The input unit 62 is configured to receive initial consumable state data of a point-of-care medical analyzer defining an initial amount of a point-of-care medical analyzer consumable present in the point-of-care medical analyzer, and an analyzer identifier at a first time index.

The input unit 62 is configured to receive a second time index.

The processing unit 64 is configured to generate predicted consumable state data defining an amount of the point-of-care medical analyzer consumable predicted to be present in the point-of-care medical analyzer at the second time index using a predicted consumable depletion model selected using at least the analyzer identifier and the initial consumable state data.

The predicted consumable depletion model comprises (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test.

The predicted consumable state data is generated by the processing unit 64 based on an aggregation of the initial amount of a point-of-care medical analyzer consumable present in the point-of-care medical analyzer, and the outputs of at least the predicted consumable depletion model and the point-of-care medical analyzer use model between the first time index and the second time index.

Accordingly, it is proposed to receive up-to-date measurements of reagents from analyzers deployed at point-of-care locations, and to project, for each analyzer, when the various reagent consumables will run-out.

The apparatus 60 may be implemented upon a wide range of computing devices. For example, a personal computer, a server, a smart-phone, a cloud server, and an embedded computer (optionally inside a point-of-care medical analyzer) may all be configured to perform as an apparatus according to the first aspect.

According to an optional embodiment of the first aspect, the apparatus 60 applies a de-vice-specific average use in order to give a more precise estimate of when the device will be usable.

The proposed framework is flexible, and optionally may integrate domain knowledge, and monitored statistics of such point-of-care medical analyzer systems to determine if an analyzer would run out of consumables over a public holiday or weekend, for example. This enables a point-of-care coordinator to order and to replace reagents in time before they run out.

Optionally, the status of all reagent consumables in the point-of-care medical analyzers may be gathered in one GUI view. This enables an operator to see which devices will experience consumable outage in the future. Optionally, the data may be visualised as a "calendar view" enabling an operator to simulate how consumable levels evolve over time, optionally based on the present level of consumables.

In other words, for each analyzer, and each type of consumable, when projecting the state of the consumables, one, or more of the following aspects may be taken into account: the current level of consumables in an analyzer (as measured using reagent sensor 28); the expiration date of the consumables, a projected number of measurements for the particular analyzer; and an average use of consumable per test.

Optionally, the information is presented on a GUI in a chronological timeline enabling a point-of-care coordinator to monitor a prediction of future events leading up to a consumable outage on an analyzer.

Optionally, the information is presented on a GUI illustrating the actual and/or predicted level of reagent remaining in a replaceable cartridge, sealed bag, or estimated remaining lifetime of a sensor cassette, for example utilizing a schematic cut-through view of a replaceable cartridge or sealed bag.

FIG. 4 illustrates a method in accordance with the second aspect. In particular, there is provided a method for generating predicted consumable state data of a point-of-care medical analyzer, comprising:

- receiving 100 initial consumable state data of a point-of-care medical analyzer defining an initial amount of a point-of-care medical analyzer consumable present in the point-of-care medical analyzer, and an analyzer identifier at a first time index;
- receiving 102 a second time index;
- generating 104 predicted consumable state data defining an amount of the point-of-care medical analyzer consumable predicted to be present in the point-of-care medical analyzer at the second time index using a predicted consumable depletion model selected using at least the analyzer identifier and the initial consumable state data;
- wherein the predicted consumable depletion model comprises (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test; and
- wherein the predicted consumable state data is generated based on an aggregation of the initial amount of a point-of-care medical analyzer consumable present in the point-of-care medical analyzer, and the outputs of at least the predicted consumable depletion model and the point-of-care medical analyzer use model between the first time index and the second time index.

Figure 5:
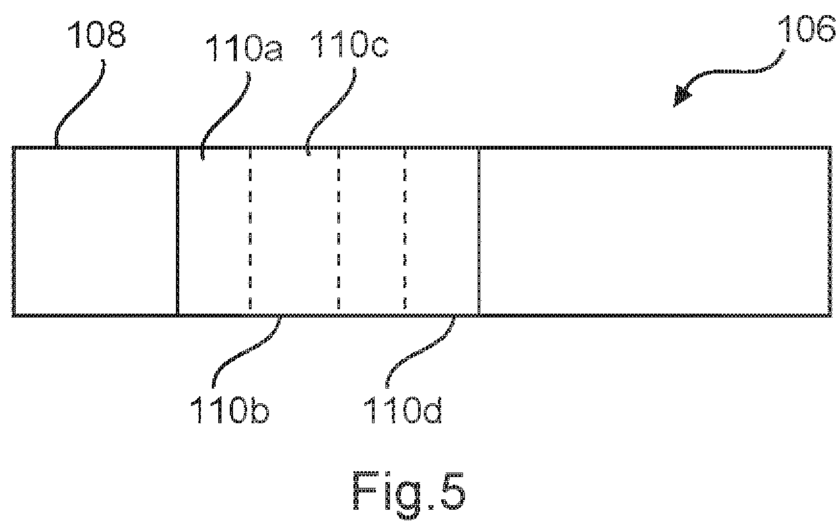
FIG. 5 schematically illustrates an example of an applicable data structure.

FIG. 5 illustrates one possible data structure 106 may be transmitted by point-of-care medical analyzers 10*x*, 10*y*, 10*z* between the point-of-care 85 and an apparatus 60 as illustrated in FIG. 2, for example. In particular, the data structure 106 encapsulates initial consumable state data transmitted from a point-of-care medical analyzer defining an initial amount of point-of-care medical analyzer consumable present in the point-of-care medical analyzer. The data structure 106 comprises a packet header 108 (which may be, for example, a TCP/IP header in addition to any application-specific software headers). Furthermore, the data structure 106 comprises a plurality of consumable state fields 110*b*, 110*c*, 110*d*. Each consumable state field comprises data measured by a reagent fluid supply monitoring unit 32, for example, defining the fill level of a reagent supply, or sealed bag, inside a point-of-care medical analyzer, or the estimated remaining lifetime of the sensor cassette.

Figure 6:
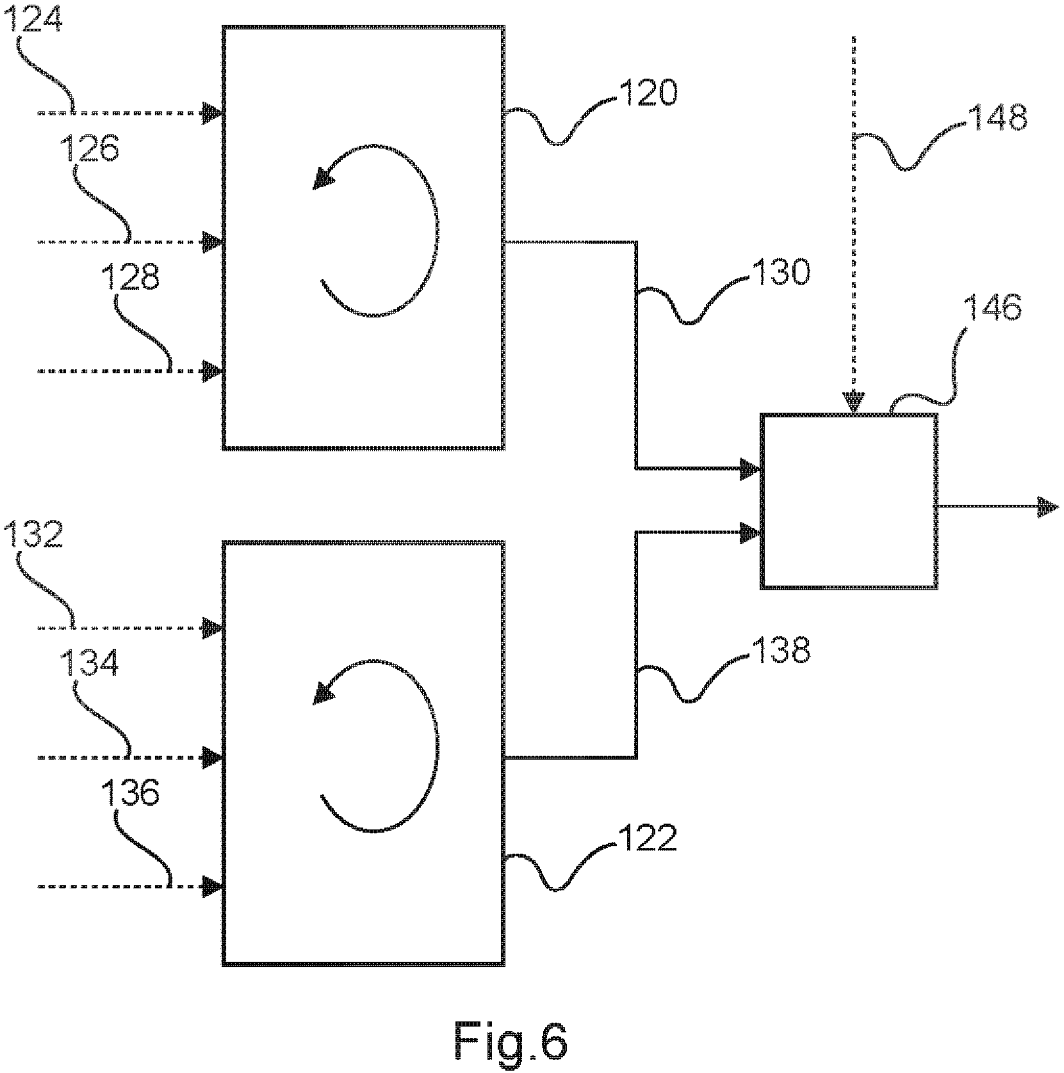
FIG. 6 schematically illustrates an algorithm for predicting consumable state.

FIG. 6 illustrates a functional diagram of the algorithm underlined the present invention. A predicted consumable depletion model defining a consumable depletion model 120 and a point-of-care medical analyzer use model 122 is illustrated.

The consumable depletion model 120 continuously tracks how one activity of the analyzer translates into consumable usage. In other words, it tracks how, for a particular point-of-care medical analyzer, one use of the point-of-care medical analyzer translates into consumable usage. This can be achieved using some constants, data from the actual consumables, as well as historical consumption information known about the specific point-of-care medical analyzer.

The consumable depletion model 120 is optionally a continuously self-correcting predictive model which optionally updates every time one input changes.

Optionally, the consumable depletion model 120 is a look-up table, defining a list of reagent volumes depleted for each type of test performed.

Optional inputs to the consumable depletion model 120 are, for example, a historic usage parameter 124, values derived from research and development 126 (such as various constants, coefficients, and rules that affect the predictions such as "when the analyzer has been operating for fewer than 23 hours, test type III uses an additional 5.6% of the consumable". Another optional input to the consumable depletion model is consumable data reported from production 128. This provides detailed information, for example, about the content and capacity of each type of consumable.

The output 130 of the consumable depletion model 120 is a volume or set of volumes defining consumable usage per activity (test) type. Optionally, the output volume or set of volumes may, for example, form an average of a statistical distribution or distribu-tions enabling the probability of the output of a given volume of reagent, per test, to be defined.

The point-of-care medical analyzer use model 122 predicts a projected number of activities and activity types for a particular point-of-care medical analyzer. The models work by calculating how the input parameters contribute to the end usage amount of the point-of-care medical analyzer. The parameters that affect the usage the most will be weighted higher, when predicting the final activities. Using the inputs and historic usage patterns, the model will predict the future usage of the analyzer, and optionally the possibility of getting the prediction right.

The point-of-care medical analyzer use model 122 is optionally a continuously self-correcting predictive model updated when its inputs change. Typical input parameters of the point-of-care medical analyzer use model 122 are historic usage pattern data 132 of a given point-of-care medical analyzer, device meta data such as the model or configuration of the point-of-care medical analyzer 134, and/or point-of-care medical analyzer location information 136 (for example, the department or hospital in which the point-of-care medical analyzer is located). The point-of-care medical analyzer use model 122 outputs a predicted number of activities between first and second time indexes 138. The aggregator 140 combines the predicted number of consumable usage per activity and the predicted number of different activities for the single device in between the first and second time indexes to yield a prediction of when a particular point-of-care medical analyzer will deplete a given reagent consumable or consumables.

The initial amount of a point-of-care medical analyzer consumable present in the point-of-care medical analyzer 148, measured by sensors inside a point-of-care medical analyzer, is input into the aggregator 140.

Optionally, the aggregator 140 may output a probabilistic estimate of when a particular point-of-care medical analyzer will deplete a given reagent consumable or consumables in between the first and second time indexes.

Optionally, the predicted consumable state data generated as described above can be updated continuously such that any time one of the inputs to the model changes, the entire system, or branch of the system will quickly adapt to those changes. This provides a system that can quickly and precisely adjust to changes in the environment that the analyzer is located in. Furthermore, because many of the inputs change frequently, the precision of the system may be affected. However according to the system described above, probabilities of prediction error data may be provided to the user.

FIG. 7 illustrates three various types of GUI (Graphical User Interface) that may be displayed to a user of an apparatus system provided according to the present application.

It will be appreciated that a wide range of output options may be provided. For example, a graphical summary of reagent state one or more point-of-care medical analyzers may be provided on a screen of a personal computer in tabular or numerical form. The graphical summary may be printed out using a printer. Furthermore, the graphical summary may be re-sized and re-arranged to enable a range of smart phone applications to display a reagent state of one or more point-of-care medical analyzers to a user. It will be appreciated in the following discussion that fewer or more point-of-care medical analyzers than those used in the illustrated examples may be provided and that the examples are for illustration only.

Figures 7A, 7B, 7C:
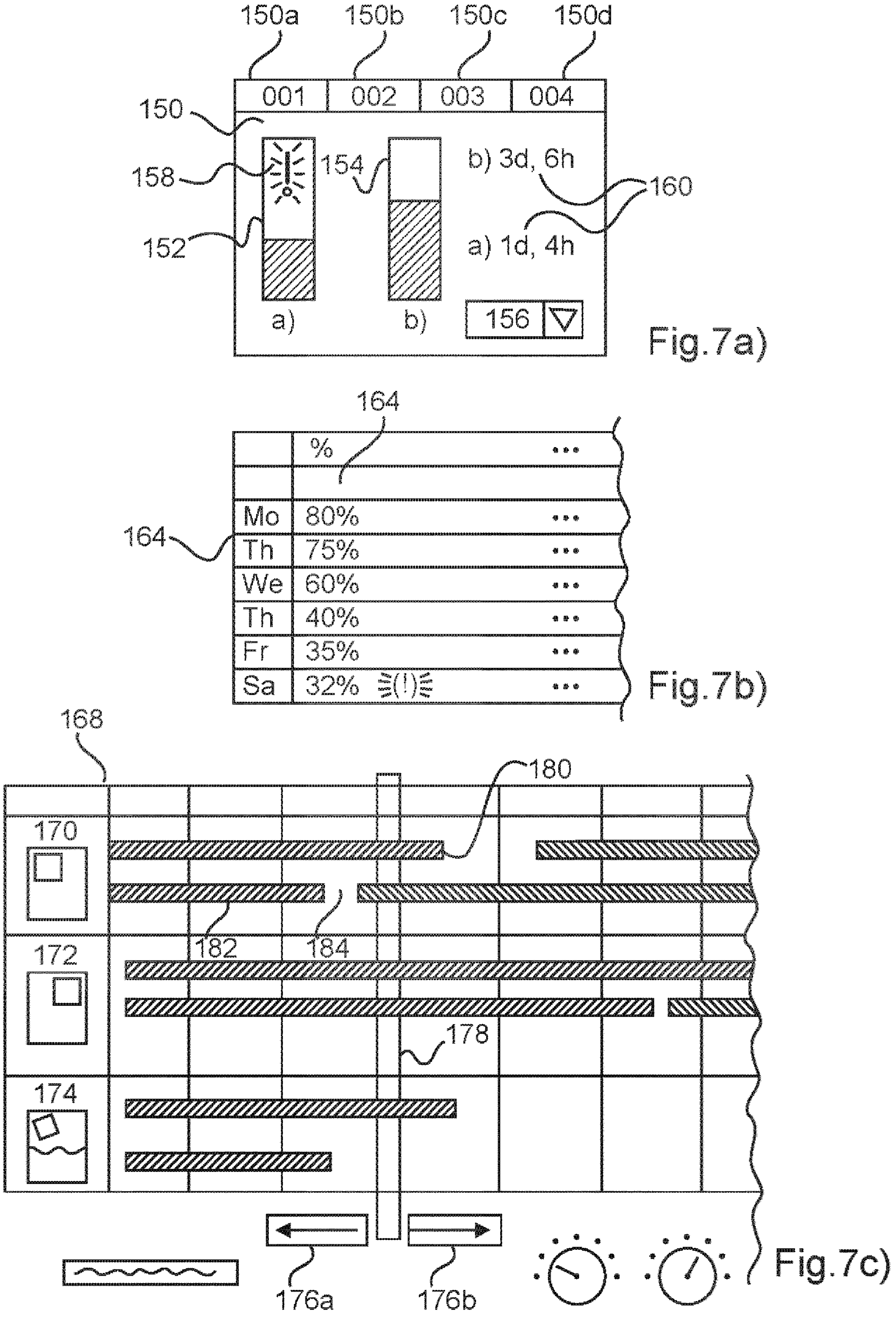
FIG. 7*a*) illustrates a variant of a graphical user interface (GUI).
FIG. 7*b*) illustrates a further variant of a GUI.
FIG. 7*c*) illustrates a yet further variant of a GUI.

FIG. 7*a*) illustrates an example of a GUI format 150 that may be displayed on a data output unit of an apparatus 60 and/or a point-of-care medical analyzer 10*x* as discussed above. This GUI is illustrated in a "tabbed" format with tabs 150*a*, 150*b*, 150*c*, and 150*d* representing the reagent states of four different point-of-care medical analyzers. The first tab 150*a* is shown with a first reagent indicator 152 and a second reagent indicator 154. Drop-down menu 156 has been used to select a second time index. A method according to the second aspect has been used to calculate the remaining amount of reagent at the second time index. Optionally, the first and second reagent indicators are bar graphs, and/or numerical time displays displaying the remaining amount of the first and second reagents inside the given point-of-care medical analyzer. Optionally, this embodiment of the GUI is configured to display warning indicator 158 if a level of the first reagent (for example) is not sufficient for a predicted workload of the point-of-care medical analyzer. Optionally, the numerical displays 160 may define the remaining time during which the given first and second reagents are available in view of the predicted workload. This display technique may be more appropriate to simple (optionally monochrome) displays on point-of-care medical analyzers.

FIG. 7*b*) illustrates a further version of a GUI format 162 that may be displayed on a data output unit of an apparatus 60 and/or a point-of-care medical analyzer 10*x* as discussed above. This GUI displays, for a given week, a tabular prediction of a percentage reagent usage 164. Such a display option is more suited to output by printing onto paper as a printed report, for example.

FIG. 7*c*) illustrates a yet further version of a GUI format 168 that may be displayed on a data output unit of an apparatus 60 and/or a point-of-care medical analyzer 10*x* as discussed above. This GUI has, on the left-hand-side three rows, with the first row 170 representing a first point-of-care medical analyzer, a second row 172 representing a second point-of-care medical analyzer, and a third row 174 representing a third point-of-care medical analyzer. The width dimension of the illustrated GUI represents earlier and later times, in the manner of a "GANTT" chart. In the illustrated case, point-of-care medical analyzers 170, 172, 174 are identical and each require a report of two reagent amounts. However, the skilled person will appreciate that the GUI may report on the amount of fewer or more reagents. Time navigation arrows 176*a* and 176*b* enable a user to "scan" a time-limit indicator 178 backwards and forwards in time, respectively.

For a first point-of-care medical analyzer 170, first bar 180 defines an availability of a first reagent. Second bar 182 defines an availability of a second reagent. Bar 182 of the first point-of-care medical analyzer 172 is interrupted at 184, illustrating a replacement of the second reagent.

Optionally, time-limit indicator 178 is set by a user to a time point on the GUI corresponding to the second time index up until which the point-of-care medical analyzers must not run out of consumables. Optionally, the rows for first point-of-care medical analyzer 170, second point-of-care medical analyzer 172, and third point-of-care medical analyzer 174 may be ordered according to how urgently consumable replacement is needed. Optionally, a "to-do list" of important point-of-care medical analyzer refill tasks approaching may be generated.

Optionally, the bars of the GUI may be configured to display as "hard" (monotone) bars, which are interrupted at time points where a guarantee of the availability of a respective reagent falls below a probability level calculated by the predicted consumable depletion model.

Optionally, the bars of the GUI may be configured to display as "variable intensity" bars in which the probability of correctness of an estimate of the predicted consumable depletion model worsens. For example, it would naturally be expected that for time periods further into the future, small errors in the predicted consumable depletion model will amplify. Displaying a higher error probability with a weaker bar intensity could emphasise to a user that reagent replacement will be necessary at a given date displayed on the GUI where the bar intensity becomes too weak.

According to a fourth aspect, there is provided a computer program element comprising instructions which, when executed by a computer, enables the computer to carry out the method of the first aspect or its embodiments.

According to a fifth aspect, there is provided a computer program product, tangibly embodied on a carrier medium, comprising software code for carrying out the method of the first aspect.

The computer program element may comprise, for example, a data structure containing computer instructions which, when executed by a processing unit of a computer, perform the calculation steps of the method of the second aspect.

The invention may be embodied on a computer that has comprised the computer program element from the beginning, or a computer that has received, by means of a disc or Internet update the computer program element in the form of an update.

Optionally, the computer readable medium may comprise an optical storage or distribution medium, such as a CD-ROM disk, a DVD, or alternatively a solid-state storage or distribution medium such as a USB stick, or a magnetic disk.

Optionally, a program for providing the computer program element via downloading over the Internet is provided.

Although the invention has been illustrated and described with reference to the drawings and this description, these should be considered to be illustrative and exemplary, rather than restrictive. The invention is not limited to the disclosed embodiments. A skilled person studying the drawings, disclosure, and dependent claims can put into practice reasonable variations to the embodiments discussed herein. The reference signs are not to be construed as limiting the scope.

The invention claimed is:

1. A computer for a point-of-care medical analyzer, the computer comprising:

an input unit; and a processing unit;

wherein the input unit is configured to receive initial consumable state data of the point-of-care medical analyzer defining an initial amount of a point-of-care medical analyzer consumable present in the point-of-care medical analyzer, and an analyzer identifier at a first time index;

wherein the input unit is configured to receive a second time index;

wherein the input unit is configured to receive usage location metadata of the point-of-care medical analyzer defined by the analyzer identifier;

wherein the point-of-care medical analyzer is configured to receive a sample taken from a patient and wherein the point-of-care medical analyzer consumable is selected from at least one of a reagent fluid and a sensor cassette, the reagent fluid and the sensor cassette being configured to contact the sample;

wherein the computer has improved analytic capability based on the processing unit being configured with prediction functionality based on a composite model comprising one or more continuously self-correcting predictive sub-models, wherein the processing unit is configured to use the prediction functionality to generate predicted consumable state data defining an amount of the point-of-care medical analyzer consumable predicted to be present in the point-of-care medical analyzer at the second time index, wherein the composite model is a predicted consumable depletion model selected using at least the analyzer identifier and the initial consumable state data;

wherein the predicted consumable depletion model comprises, as sub-models of the composite model (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test, wherein the consumable model of the point-of-care medical analyzer and/or the point-of-care medical analyzer use model are continuously self-correcting predictive models which are updated when its input parameters change, and wherein the consumable model correlates the usage location metadata with historically stored reagent depletion models;

wherein the consumable model of the point-of-care medical analyzer includes a data analysis model selected based on a point-of-care medical analyzer network type, the data analysis model being selected from one or more of a linear model, a rule-based machine learning system, experimentally fitted data, and a Bayesian model; and wherein the predicted consumable state data is generated by the processing unit based on an aggregation of the initial consumable state data defining the initial amount of the point-of-care medical analyzer consumable present in the point-of-care medical analyzer, and the outputs of at least the consumable model and the point-of-care medical analyzer use model between the first time index and the second time index.

2. The computer according to claim 1, wherein the processing unit is further configured to:

receive historic usage data of the point-of-care medical analyzer defined by the analyzer identifier.

3. The computer according to claim 1, further configured to:

generate the consumable model based on at least one of historic usage data of the point-of-care medical analyzer defined by the analyzer identifier, a consumable handling model of the point-of-care medical analyzer, a consumable usage rule set defining the consumption of the point-of-care medical analyzer consumable over time, and a consumable capacity metric of the point-of-care medical analyzer identified by the analyzer identifier and running from the initial consumable state data collected at the first time index.

4. The computer according to claim 1, further configured to: receive usage pattern data of the point-of-care medical analyzer defined by the analyzer identifier obtained before the first time index.

5. The computer according to claim 1, further configured to: receive a future usage plan of the point-of-care medical analyzer defined by the analyzer identifier between the first time index and the second time index.

6. The computer according to claim 1, further configured to: generate the point-of-care medical analyzer use model based on at least one of usage pattern data of point-of-care medical analyzer defined by the analyzer identifier obtained before the first time index, the usage location metadata, and a future usage plan of the point-of-care medical analyzer defined by the analyzer identifier between the first time index and the second time index.

7. The computer according to claim 6, wherein the point-of-care medical analyzer use model outputs an expected number of tests between the first and second time indexes.

8. The computer according to claim 7:

wherein aggregating the outputs of at least the predicted consumable depletion model and the point-of-care medical analyzer use model between the first time index and the second time index comprises:

calculating a test depletion of a point-of-care medical analyzer consumable in the point-of-care medical analyzer for a test, and multiplying the test depletion by the expected number of tests to generate the predicted consumable state data at the second time index, and/or as a variable between the first time index and the second time index.

9. The computer according to claim 1, further configured to:

receive expiry date data of the point-of-care medical analyzer consumable; and include the point-of-care medical analyzer consumable as a factor in the consumable model only between the first time index and an expiry date defined in the expiration date data.

10. A method for improving and using analytic capability of a computer for a point-of-care medical analyzer with models, the method comprising:

improving the computer's analytic capability based on configuring the computer with prediction functionality using a composite model, wherein the composite model comprises one or more continuously self-correcting predictive sub-models;

receiving initial consumable state data of the point-of-care medical analyzer defining an initial amount of a point-of-care medical analyzer consumable present in the point-of-care medical analyzer, and an analyzer identifier at a first time index;

receiving a second time index;

receiving usage location metadata of the point-of-care medical analyzer defined by an analyzer identifier; and using the improved analytic capability to generate predicted consumable state data defining an amount of the point-of-care medical analyzer consumable predicted to be present in the point-of-care medical analyzer at the second time index using, as the composite model, a predicted consumable depletion model selected using at least the analyzer identifier and the initial consumable state data;

wherein the point-of-care medical analyzer is configured to receive a sample taken from a patient and wherein the point-of-care medical analyzer consumable is selected from at least one of a reagent fluid and a sensor cassette, the reagent fluid and the sensor cassette being configured to contact the sample;

wherein the predicted consumable depletion model comprises, as sub-models of the composite model (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test, wherein the consumable model of the point-of-care medical analyzer and/or the point-of-care medical analyzer use model are continuously self-correcting predictive models which are updated when its input parameters change, and wherein the consumable model correlates the usage location metadata with historically stored reagent depletion models;

wherein the consumable model of the point-of-care medical analyzer includes a data analysis model selected based on a point-of-care medical analyzer network type, the data analysis model being selected from one or more of a linear model, a rule-based machine learning system, experimentally fitted data, and a Bayesian model; and wherein the predicted consumable state data is generated based on an aggregation of the initial consumable state data defining the initial amount of the point-of-care medical analyzer consumable present in the point-of-care medical analyzer, and the outputs of at least the consumable model and the point-of-care medical analyzer use model between the first time index and the second time index.

11. A system computer for a point-of-care medical analyzer, the computer comprising:

an input unit; and a processing unit;

wherein the input unit is configured to receive initial consumable state data of the point-of-care medical analyzer, wherein the point-of-care medical analyzer is from at least one point-of-care medical analyzer, and wherein the initial consumable state data defines an initial amount of a point-of-care medical analyzer consumable present in the point-of-care medical analyzer, and an analyzer identifier at a first time index;

wherein the input unit is configured to receive a second time index;

wherein the computer is configured to receive usage location metadata of the point-of-care medical analyzer defined by the analyzer identifier;

wherein the point-of-care medical analyzer is configured to receive a sample taken from a patient and wherein the point-of-care medical analyzer consumable is selected from at least one of a reagent fluid and a sensor cassette, the reagent fluid and the sensor cassette being configured to contact the sample;

wherein the computer has improved analytic capability based on the processing unit being configured with prediction functionality based on a composite model comprising one or more continuously self-correcting predictive sub-models, wherein the processing unit is configured to use the prediction functionality to generate predicted consumable state data defining an amount of the point-of-care medical analyzer consumable predicted to be present in the point-of-care medical analyzer at the second time index; wherein the composite model is a predicted consumable depletion model selected using at least the analyzer identifier and the initial consumable state data;

wherein the predicted consumable depletion model comprises, as sub-models of the composite model (i) a consumable model of the point-of-care medical analyzer defining a consumable depletion rate of the point-of-care medical analyzer consumable in the point-of-care medical analyzer for a test, and (ii) a point-of-care medical analyzer use model defining an occurrence rate of the test, wherein the consumable model of the point-of-care medical analyzer and/or the point-of-care medical analyzer use model are continuously self-correcting predictive models which are updated when its input parameters change, and wherein the consumable model correlates the usage location metadata with historically stored reagent depletion;

wherein the consumable model of the point-of-care medical analyzer includes a data analysis model selected based on a point-of-care medical analyzer network type, the data analysis model being selected from one or more of a linear model, a rule-based machine learning system, experimentally fitted data, and a Bayesian model;

wherein the predicted consumable state data is generated by the processing unit based on an aggregation of the initial amount of the point-of-care medical analyzer consumable present in the point-of-care medical analyzer, and the outputs of at least the consumable model and the point-of-care medical analyzer use model between the first time index and the second time index and being further configured to receive usage location metadata of the point-of-care medical analyzer defined by the analyzer identifier; and wherein the point-of-care medical analyzer is configured to transmit to the computer, via a data communications network, initial consumable state data of a point-of-care medical analyzer defining the initial amount of the point-of-care medical analyzer consumable present in the point-of-care medical analyzer, and an analyzer identifier at the first time index.

12. The computer according to claim 11, further comprising:

a mobile data terminal;

wherein the mobile data terminal is configured to:

display a GUI comprising a representation of the point-of-care medical analyzer, and the initial amount of the point-of-care medical analyzer consumable present in the point-of-care medical analyzer;

transmit to the processing unit, via the data network, the second time index via the GUI interface;

receive response data from the processing unit; and display an indication of how urgently a replacement of the point-of-care medical analyzer consumable present in the point-of-care medical analyzer at the second time index is required on the GUI of the mobile device.

13. The method according to claim 10, wherein the at least one point-of-care medical analyzer is configured to identify an installed point-of-care medical analyzer consumable using a point-of-care medical analyzer consumable identifier; and wherein the at least one point-of-care medical analyzer is configured to transmit an intermediate amount of a point-of-care medical analyzer consumable present in the installed point-of-care medical analyzer consumable over the data communications network in association with the point-of-care medical analyzer consumable identifier.

14. The computer of claim 1, wherein the computer comprises an output display is configured to display, via a graphical user interface, a plurality of representations corresponding to a unique point-of-care medical analyzer of a plurality of point-of-care medical analyzers and sort the plurality of representations based on a level of urgency of replacement of each unique point-of-care medical analyzer.

15. The computer of claim 1, wherein the computer comprises an output display which is configured to display, via a graphical user interface, a remaining capacity of the point-of-care medical analyzer.

16. The computer of claim 1, wherein the point-of-care medical analyzer is configured to dynamically determine the usage location metadata after being moved from a first location to a second location.

17. The computer of claim 16, wherein the processing unit is configured to update the consumable model of the point-of-care medical analyzer based on correlating historically stored reagent depletion models with usage location metadata for the second location.

18. The method of claim 10, wherein:

the point-of-care medical analyzer is located at a first location when a first act is performed, wherein the first act is generating predicted consumable state data defining the amount of the point-of-care medical analyzer consumable predicted to be present in the point-of-care medical analyzer at the second time index; and the method comprises:

a second act, wherein the second act is moving the point-of-care medical analyzer from the first location to a second location and, a third act, wherein the third act is, based on the point-of-care medical analyzer being moved to the second location, the point-of-care medical analyzer dynamically determining the usage location metadata.

19. The method of claim 18, wherein the method comprises a fourth act, wherein the fourth act is automatically updating the consumable model of the point-of-care medical analyzer based on correlating historically stored reagent depletion models with usage location metadata.

20. The method of claim 19, wherein:

the second act, the third act and the fourth act are all performed after the first act and prior to the second time index; and the method comprises generating update predicted consumable state data defining an amount of the point-of-care medical analyzer consumable predicted to be present in the point-of-care medical analyzer at the second time index using the automatically updated consumable model.

* * * * *